(12) United States Patent
Divincenzo et al.

(10) Patent No.: US 10,441,326 B2
(45) Date of Patent: Oct. 15, 2019

(54) DRIVER INSTRUMENTS AND RELATED METHODS

(71) Applicant: Medos International Sarl, Le Locle (CH)

(72) Inventors: John Divincenzo, Braintree, MA (US); Thomas Martin, Riverside, RI (US); Nicholas Pavento, North Attleboro, MA (US); James Murray, Raynham, MA (US)

(73) Assignee: Medos International Sérl, Le Locle (CH)

( * ) Notice: Subject to any disclaimer, the term of this patent is extended or adjusted under 35 U.S.C. 154(b) by 17 days.

(21) Appl. No.: 15/389,587

(22) Filed: Dec. 23, 2016

(65) Prior Publication Data
US 2018/0177536 A1 Jun. 28, 2018

(51) Int. Cl.
*A61B 17/70* (2006.01)
*A61B 17/88* (2006.01)

(52) U.S. Cl.
CPC ...... *A61B 17/7082* (2013.01); *A61B 17/7091* (2013.01); *A61B 17/8888* (2013.01); *A61B 17/7083* (2013.01)

(58) Field of Classification Search
CPC ............ A61B 17/7082; A61B 17/7083; A61B 17/7091
See application file for complete search history.

(56) References Cited

U.S. PATENT DOCUMENTS

| | | | |
|---|---|---|---|
| 5,431,660 A | 7/1995 | Burke | |
| 5,573,530 A | 11/1996 | Fleury et al. | |
| 5,645,546 A | 7/1997 | Fard | |
| 5,741,268 A | 4/1998 | Schutz | |
| 6,189,422 B1 | 2/2001 | Stihl | |
| 6,415,693 B1 | 7/2002 | Simon et al. | |
| 6,854,742 B2 | 2/2005 | Salyer et al. | |
| 7,326,198 B2 | 2/2008 | Desarzens et al. | |
| 8,087,329 B2 | 1/2012 | Schumacher et al. | |
| 8,486,084 B2 | 7/2013 | Huene | |
| 8,814,880 B2 | 8/2014 | McAllister et al. | |
| 8,974,494 B2 | 3/2015 | Paulk et al. | |
| 9,220,542 B2 | 12/2015 | Kerboul et al. | |
| 2004/0158247 A1 | 8/2004 | Sitiso et al. | |

(Continued)

FOREIGN PATENT DOCUMENTS

WO 2014/091454 A1 6/2014

OTHER PUBLICATIONS

International Search Report and Written Opinion for Application No. PCT/US17/62689, dated Feb. 22, 2018 (9 Pages).

*Primary Examiner* — Lynnsy M Summitt
*Assistant Examiner* — Tara Rose E Carter
(74) *Attorney, Agent, or Firm* — Nutter McClennen & Fish LLP

(57) ABSTRACT

Driver instruments and related methods are disclosed herein, e.g., for applying a fastener to a bone anchor. Various features are disclosed for retaining the fastener to the driver instrument, such as tapered drive tips, as are various features for impacting the driver instrument into the fastener, such as slidable slap-hammer type handles. Driver instruments with interchangeable handles or handle geometries that can be changed without separating the instrument from an attached fastener are also disclosed.

17 Claims, 13 Drawing Sheets

(56) References Cited

U.S. PATENT DOCUMENTS

| | | | |
|---|---|---|---|
| 2005/0149053 A1* | 7/2005 | Varieur | A61B 17/7086 606/104 |
| 2006/0178673 A1 | 8/2006 | Curran | |
| 2006/0184174 A1 | 8/2006 | Harris et al. | |
| 2007/0106283 A1 | 5/2007 | Garcia et al. | |
| 2008/0045970 A1* | 2/2008 | Saidha | A61B 17/7032 606/104 |
| 2009/0005814 A1* | 1/2009 | Miller | A61B 17/7037 606/246 |
| 2009/0255383 A1 | 10/2009 | Hsieh | |
| 2010/0298838 A1 | 11/2010 | Walters | |
| 2015/0359572 A1 | 12/2015 | Reimels et al. | |

* cited by examiner

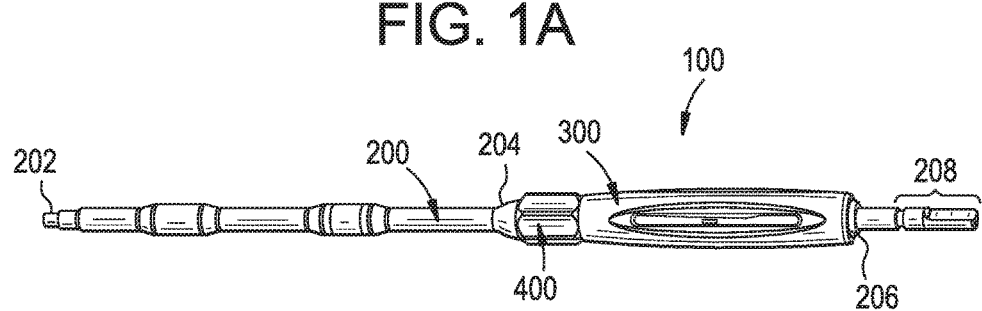
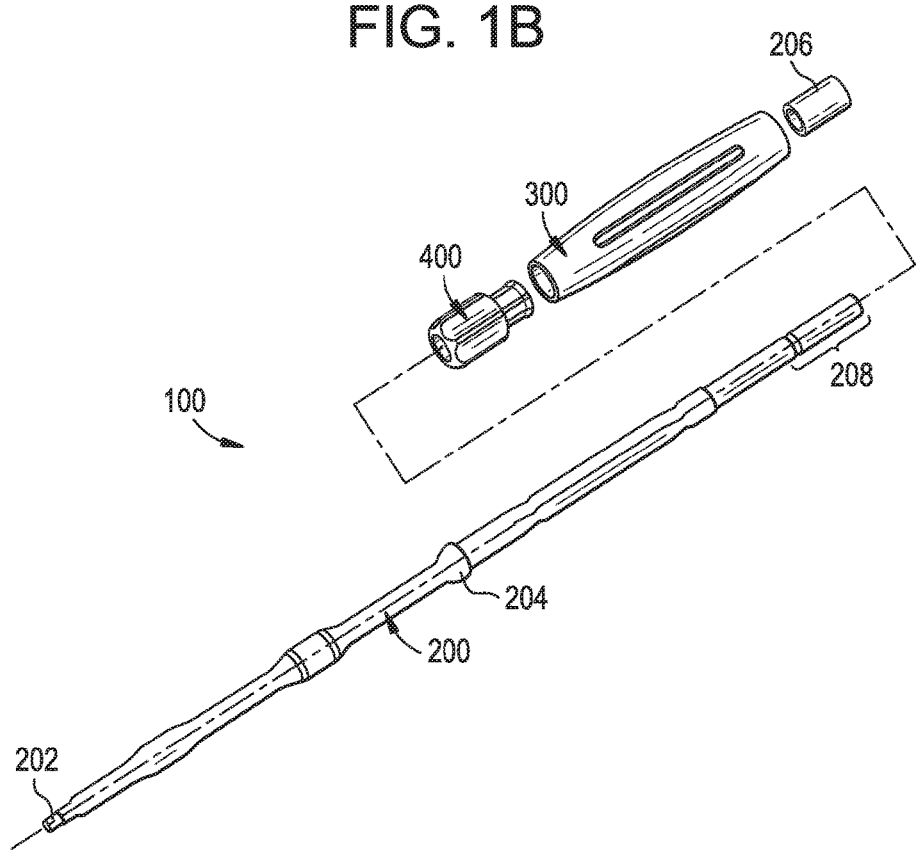

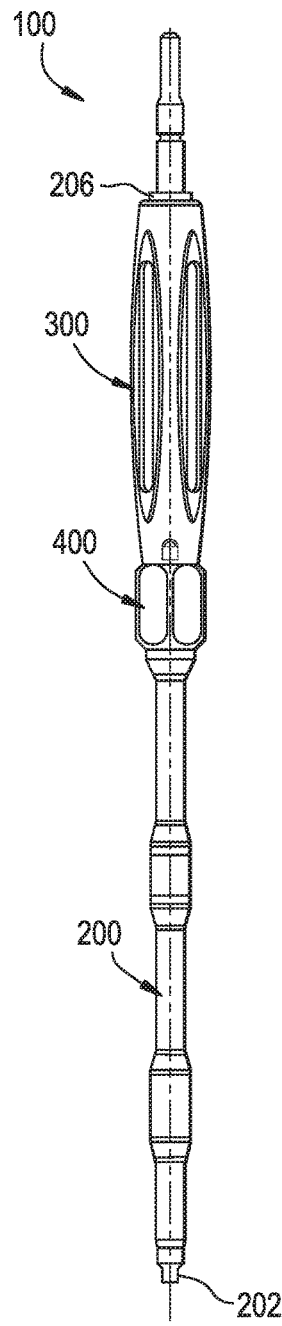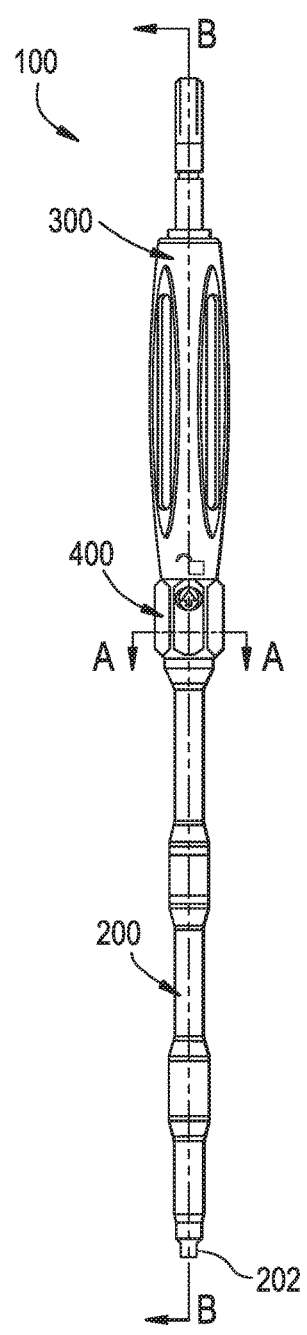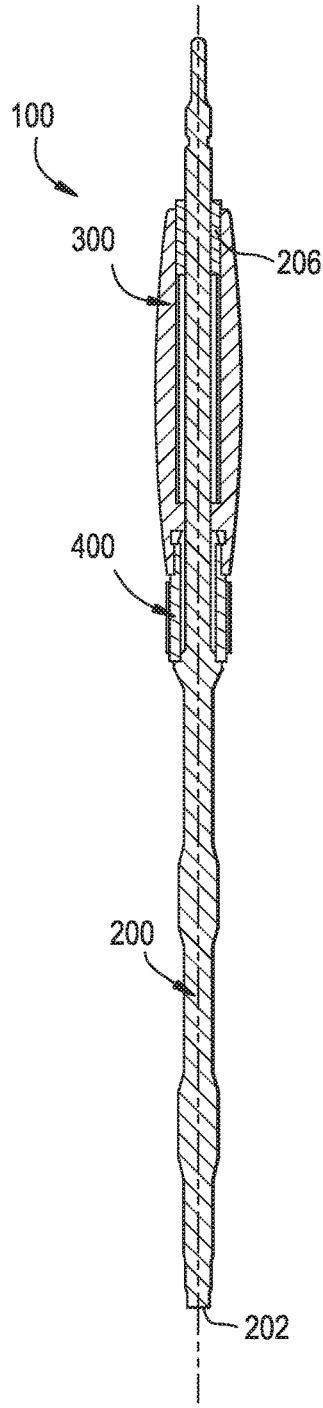

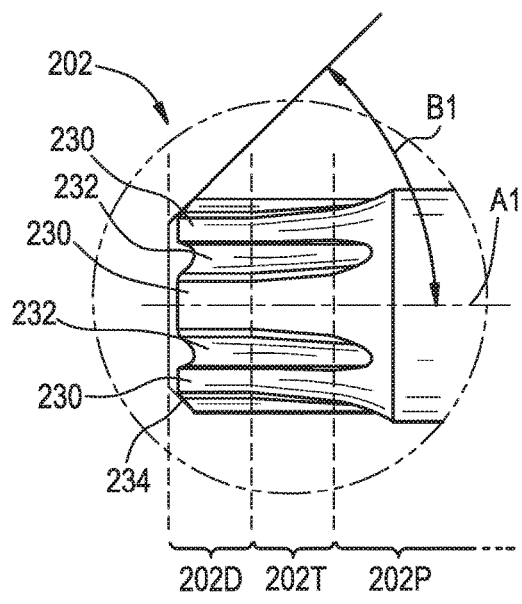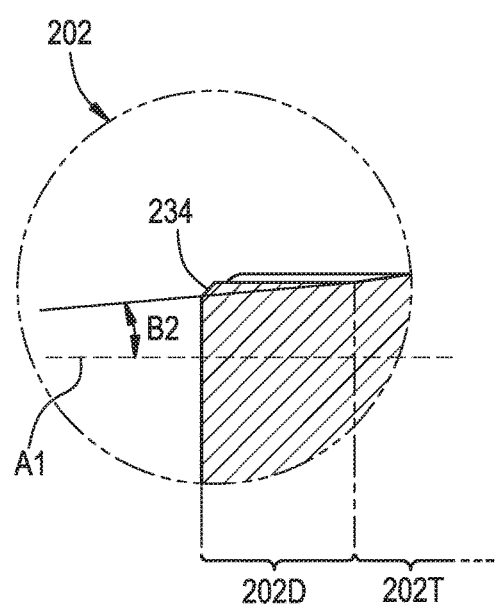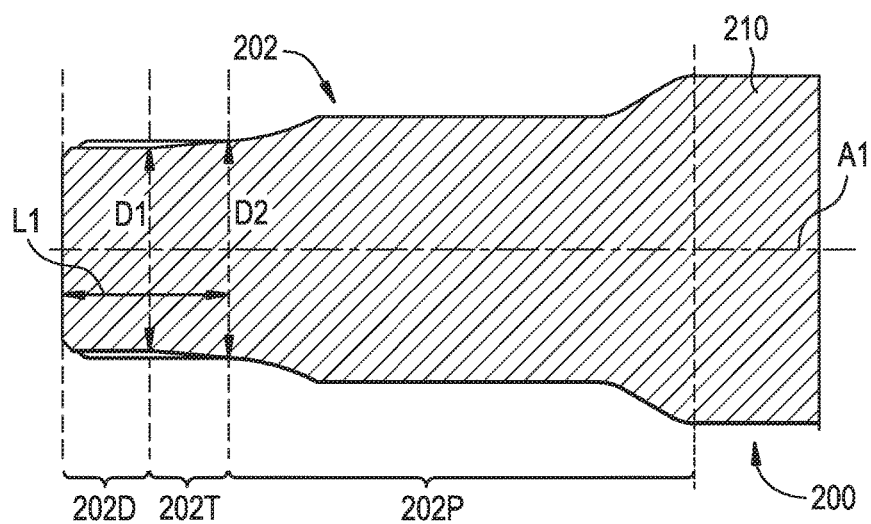

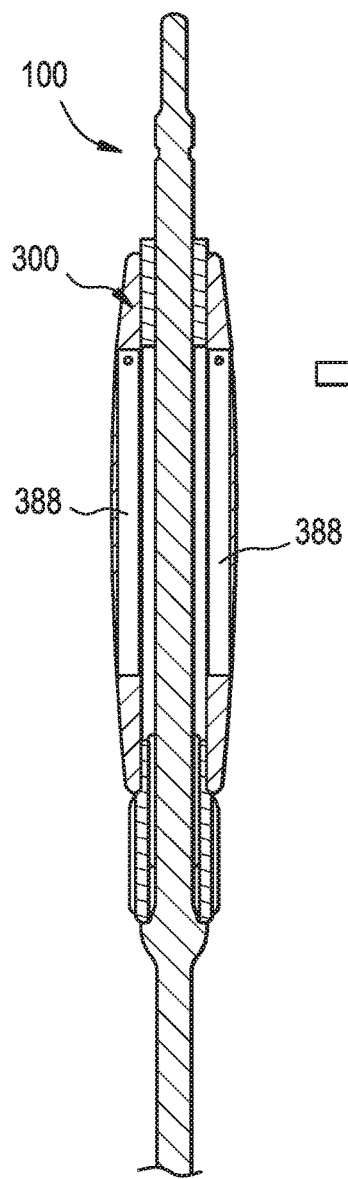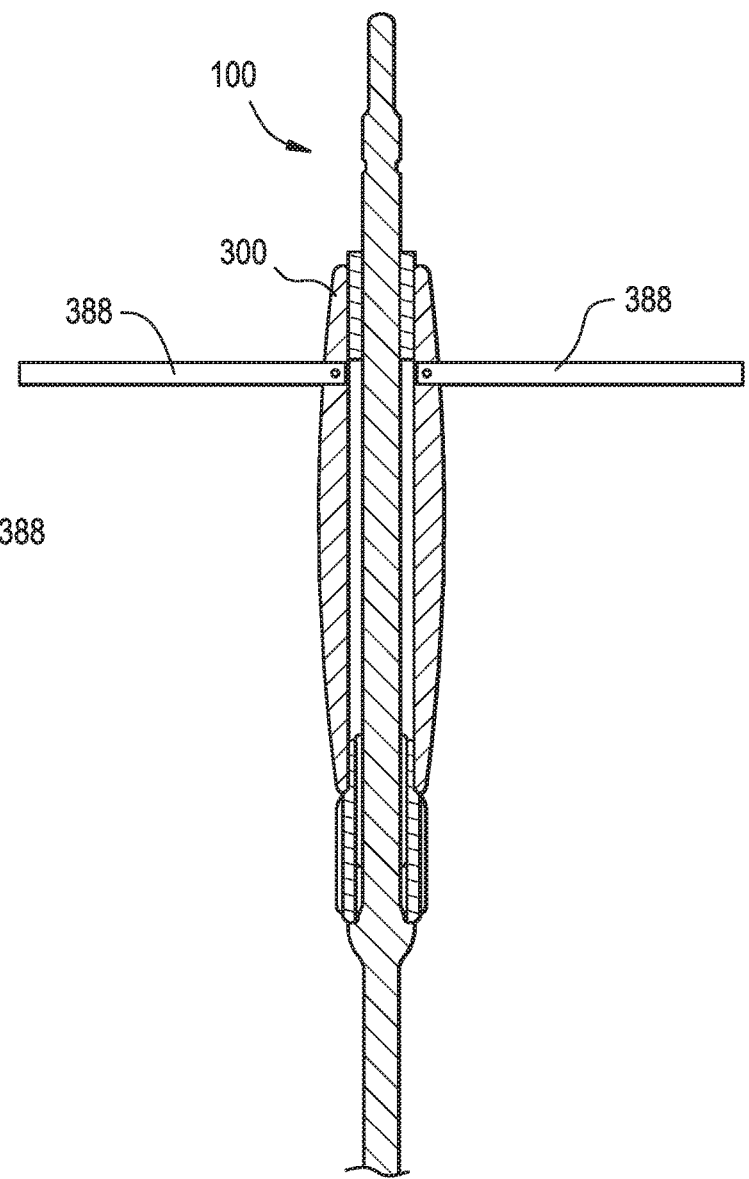

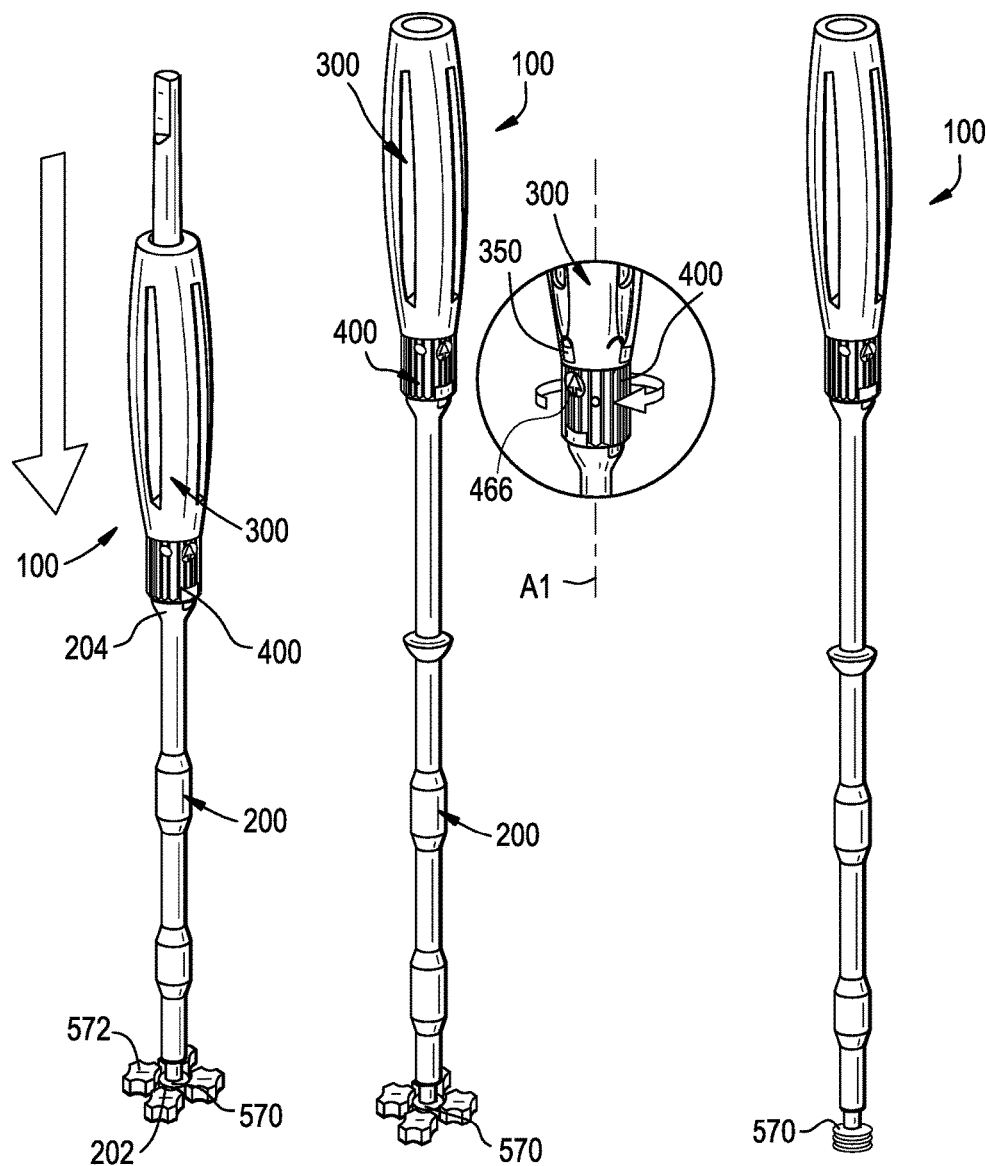

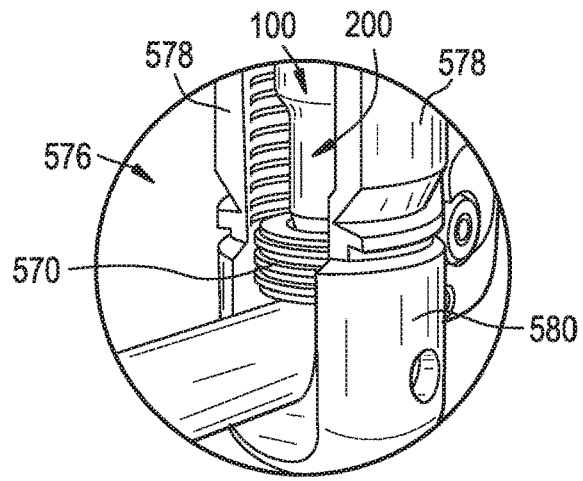
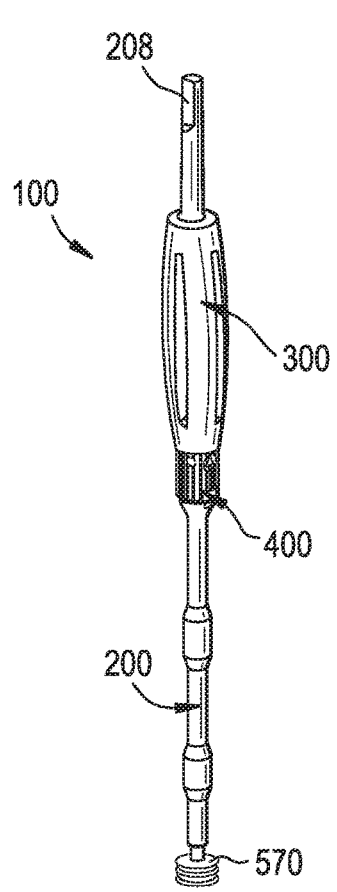
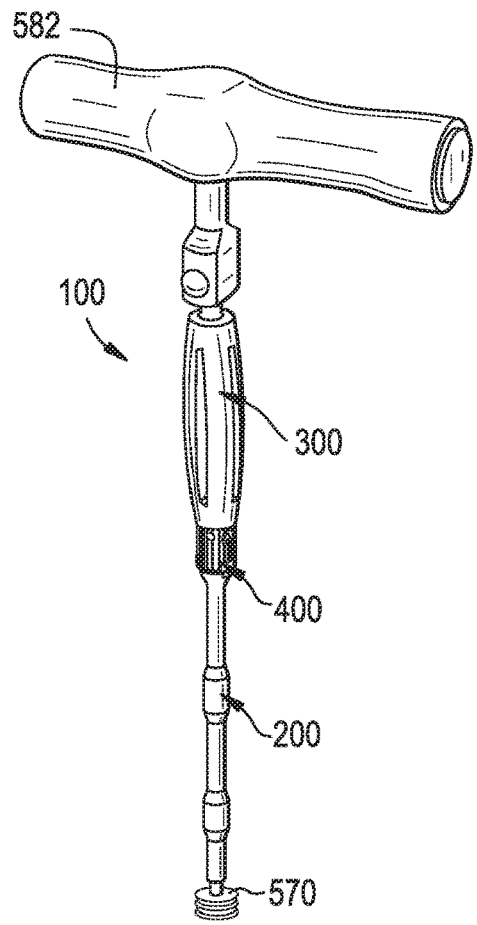

DRIVER INSTRUMENTS AND RELATED METHODS

FIELD

Driver instruments and related methods are disclosed herein, e.g., for applying a fastener to a bone anchor.

BACKGROUND

Bone anchors can be used in orthopedic surgery to fix bone during healing, fusion, or other processes. In spinal surgery, for example, bone anchors can be used to secure a rod or other spinal fixation element to one or more vertebrae to rigidly or dynamically stabilize the spine.

A fastener is typically applied to the bone anchor to reduce the rod into a rod seat of the bone anchor, to secure the rod to the bone anchor, or to lock one or more degrees of freedom of the bone anchor. Exemplary fasteners include set screws that are threaded into a proximal end of the bone anchor and closure caps that are secured to the bone anchor by quarter-turn rotation. A driver instrument is generally used to apply the fastener by applying a rotation force to the fastener.

When installing the fastener, the surgeon must be careful not to drop the fastener into the surgical site, particularly in the case of minimally-invasive procedures where it can be difficult to retrieve a dropped fastener. Driver instruments with a split tip or a retention spring have been developed to prevent the fastener from separating from the driver instrument, however such instruments may not be conducive to applying the high levels of torque needed to achieve final tightening of the fastener. Instead, the surgeon must typically switch to a solid-tipped driver instrument before final tightening. Also, in the case of threaded fasteners, handle designs that facilitate application of high levels of torque for final tightening may not be the most ergonomic design for quickly advancing the fastener along the threads during intermediate tightening. Accordingly, surgeons often use three or more different drivers for applying the fastener: a first driver for initial placement of the fastener, a second driver for intermediate tightening of the fastener, and a third driver for final tightening. This can make installing the fastener cumbersome and time-consuming, potentially leading to surgeon fatigue, poor ergonomics, and lengthened surgical times.

SUMMARY

Driver instruments and related methods are disclosed herein, e.g., for applying a fastener to a bone anchor. Various features are disclosed for retaining the fastener to the driver instrument, such as tapered drive tips, as are various features for impacting the driver instrument into the fastener, such as slidable slap-hammer type handles. Driver instruments with interchangeable handles or handle geometries that can be changed without separating the instrument from an attached fastener are also disclosed.

In some embodiments, a method of applying a fastener to a bone anchor includes inserting a drive tip of a driver instrument into a drive recess of the fastener; applying an axial force to a driver shaft of the instrument to impact the drive tip into the drive recess of the fastener and retain the fastener to the drive tip by an interference fit; positioning the instrument and the fastener retained thereto with respect to a bone anchor; and rotating a handle of the instrument to rotate the driver shaft and apply the fastener to the bone anchor.

The fastener can be a set screw. Applying the fastener can include threading the set screw into opposed threaded arms of the bone anchor to retain a spinal rod within the bone anchor. Applying the axial force can include sliding a handle of the instrument distally along the driver shaft to exert an axial force on a shoulder of the driver shaft. Retaining the fastener can include wedging a tapered portion of the drive tip within the drive recess of the fastener. The tapered portion can taper continuously from a reduced distal diameter to an enlarged proximal diameter. The drive recess of the fastener can have a diameter that is greater than or equal to the reduced distal diameter and less than the enlarged proximal diameter. The method can include locking the handle at a fixed longitudinal position along the driver shaft. Locking the handle can include rotating a locking collar coupled to the handle with respect to the handle about a central longitudinal axis of the driver shaft to a locked position. When the locking collar is in the locked position, a projection formed in a central passage of the locking collar can be received within a corresponding recess formed in the driver shaft to prevent longitudinal translation of the locking collar relative to the driver shaft. When the locking collar is in the locked position, an indicator finger of the locking collar can be received within a first groove formed in the handle to maintain the locking collar in the locked position and provide an indication to a user that the locking collar is in the locked position. The method can include unlocking the handle from a fixed longitudinal position along the driver shaft. Unlocking the handle can include rotating a locking collar coupled to the handle with respect to the handle about a central longitudinal axis of the driver shaft to an unlocked position. When the locking collar is in the unlocked position, a projection formed in a central passage of the locking collar can be positioned outside of a corresponding recess formed in the driver shaft to allow longitudinal translation of the locking collar relative to the driver shaft. When the locking collar is in the unlocked position, an indicator finger of the locking collar can be received within a second groove formed in the handle to maintain the locking collar in the unlocked position and provide an indication to a user that the locking collar is in the unlocked position. The method can include rotating a locking collar of the instrument to lock or unlock a longitudinal position of the handle with respect to the driver shaft. Rotating the locking collar can include rotating a plurality of retention fingers extending from the locking collar within an annular groove formed in the handle. The method can include, without separating the driver shaft from the fastener, sliding the handle to a distal position along the driver shaft, attaching a second handle to a proximal end of the driver shaft, and rotating the second handle to further tighten the fastener to the bone anchor.

In some embodiments, an instrument for applying a fastener to a bone anchor includes a driver shaft having a proximal end and a distal end that define a central longitudinal axis extending therebetween, the distal end of the driver shaft including a drive tip; a handle non-rotatably coupled to the driver shaft; and a locking collar having an unlocked position in which the locking collar and the handle are free to translate longitudinally along the driver shaft and a locked position in which the locking collar and the handle are maintained at a fixed longitudinal position along the driver shaft; wherein the handle is slidable along the driver shaft when the locking collar is in the unlocked position to apply an axial force to the driver shaft to impact the drive tip into a drive recess of a fastener and thereby retain the fastener to the drive tip.

The drive tip can be tapered and can be configured to frictionally retain a fastener thereto. The drive tip can taper continuously from a reduced distal cross-section to an enlarged proximal cross-section. The drive tip can include a distal section that defines a ramped lead-in surface, an intermediate tapered section that tapers from a smaller distal diameter to a larger proximal diameter, and a proximal section that transitions from the larger proximal diameter to a diameter of a body of the driver shaft. The instrument can include a fastener having a non-tapered drive recess in which the tapered drive tip is received. The locking collar can be movable from the unlocked position to the locked position and from the locked position to the unlocked position by rotating the locking collar with respect to the handle about the central longitudinal axis of the driver shaft. The locking collar can be attached to the handle by a plurality of retention fingers extending from the locking collar and received within an annular groove formed in the handle. The locking collar can include an indicator finger extending from the locking collar and selectively received within first and second grooves formed in the handle corresponding to the locked and unlocked positions, respectively. The first and second grooves can be spaced about a circumference of an interior sidewall of the handle. The indicator finger can include a radial projection that is axially offset from radial projections of retention fingers that attach the locking collar to the handle. The driver shaft can include one or more reliefs configured to receive the indicator finger as the indicator finger is deformed radially-inward during transition of the locking collar from the locked position to the unlocked position. The locking collar can include a projection that is received within a corresponding recess of the driver shaft when the locking collar is in the locked position and that is offset from the corresponding recess of the driver shaft when the locking collar is in the unlocked position. The driver shaft can include a modular handle coupling at a proximal end thereof. The driver shaft can include a shoulder that defines a proximal-facing impact surface against which the locking collar can be urged to apply a distally-directed force to the driver shaft. The driver shaft can include a distal recess in which a portion of the locking collar can be received to lock the handle in a distal position and a proximal recess in which the portion of the locking collar can be received to lock the handle in a proximal position. The handle can include at least one arm deployable therefrom. The drive tip can include a spring configured to urge the drive tip out of engagement with a fastener when the fastener is coupled to the drive tip.

BRIEF DESCRIPTION OF THE DRAWINGS

FIG. 1A is a perspective view of a driver instrument;
FIG. 1B is an exploded perspective view of the instrument of FIG. 1A;
FIG. 1C is a side view of the instrument of FIG. 1A;
FIG. 1D is a top view of the instrument of FIG. 1A;
FIG. 1E is a sectional side view of the instrument of FIG. 1A;
FIG. 2C is a detail side view of a drive tip of the instrument of FIG. 1A;
FIG. 2D is a detail sectional side view of the drive tip of FIG. 2C;
FIG. 2E is another detail sectional side view of the drive tip of FIG. 2C;
FIG. 3F is a sectional side view of the instrument of FIG. 1A, shown with a deployable handle in a retracted position;
FIG. 3G is a sectional side view of the instrument of FIG. 1A, shown with a deployable handle in a deployed position;
FIG. 5C is a perspective view of the instrument of FIG. 1A being impacted distally into the fastener of FIG. 5A;
FIG. 5D is a perspective view of the locking collar of the instrument of FIG. 1A rotated to a locked position;
FIG. 5E is a perspective view of the instrument of FIG. 1A with a fastener coupled thereto;
FIG. 5G is a perspective view of the drive tip of the instrument of FIG. 1A driving a fastener into a bone anchor;
FIG. 5H is a perspective view of the instrument of FIG. 1A with the handle in a distal position;
and
FIG. 5I is a perspective view of the instrument of FIG. 1A with a T-handle attached thereto.

DETAILED DESCRIPTION

Figure 2A:
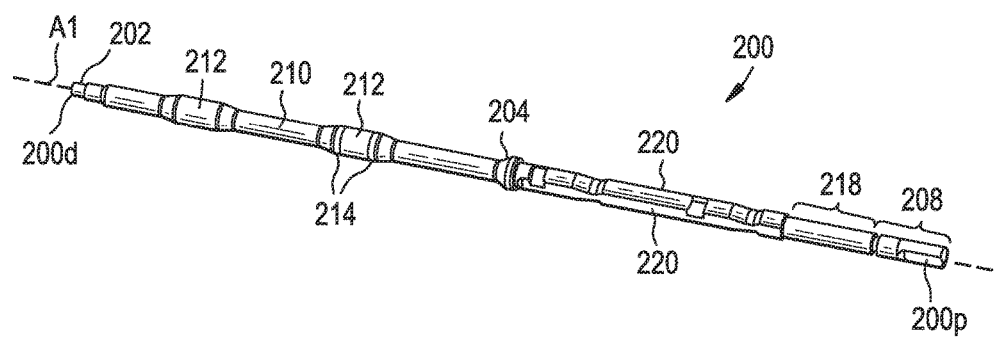
FIG. 2A is a perspective view of a driver shaft of the instrument of FIG. 1A.

Driver instruments and related methods are disclosed herein, e.g., for applying a fastener to a bone anchor. Various features are disclosed for retaining the fastener to the driver instrument, such as tapered drive tips, as are various features for impacting the driver instrument into the fastener, such as slidable slap-hammer type handles. Driver instruments with interchangeable handles or handle geometries that can be changed without separating the instrument from an attached fastener are also disclosed.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1A-1E illustrate an exemplary embodiment of a driver instrument 100 that can be used, for example, to apply a fastener to a bone anchor. As shown, the instrument 100 can include a driver shaft 200, a handle 300, and a locking collar 400. A drive tip 202 can be formed at the distal end of the driver shaft 200 and can be configured to facilitate retention of a fastener to the instrument 100. In the illustrated embodiment, the drive tip 202 is tapered such that an axial force applied to the driver shaft 200 is effective to wedge the drive tip into a drive recess of a fastener to releasably retain the fastener to the instrument 100. The handle 300 can be longitudinally-slidable along the driver shaft 200 between a distal limit and a proximal limit. The distal limit can be defined by a shoulder portion 204 of the driver shaft 200. The proximal limit can be defined by an assembly sleeve or ring 206, which can be affixed to the driver shaft 200 by welding or other techniques after the handle 300 and locking collar 400 are assembled to the driver shaft. The handle 300 can be slid distally against the shoulder 204 to apply an axial force to the driver shaft 200 and impact the drive tip 202 into the fastener. The handle 300 can be rotatably fixed to the driver shaft 200 to allow torque applied to the handle to be transferred to the driver shaft and the fastener. The locking collar 400 can be configured to selectively lock the handle 300 at one or more longitudinal positions along the driver shaft 200.

In use, the locking collar 400 can be moved to an unlocked position, the driver shaft 200 can be positioned over a fastener, and the handle 300 can be slid distally along the driver shaft to impact the drive tip 202 into the fastener and thereby retain the fastener to the instrument 100. The handle 300 can then be returned to a proximal position and locked in place using the locking collar 400, at which time the instrument 100 can be used to apply the fastener to a bone anchor. The handle 300 can also be locked in a distal position to expose a modular coupling 208 for attaching different handles to the driver shaft 200, including handles configured to apply high torque levels to the driver shaft.

Figure 2B:
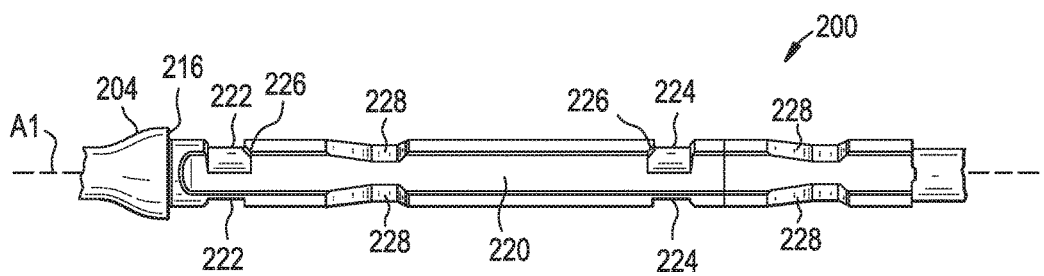
FIG. 2B is a detail side view of the driver shaft of FIG. 2A.

The driver shaft 200 is shown in greater detail in FIGS. 2A-2B. As shown, the driver shaft 200 can include an elongate, generally-cylindrical body 210 having a proximal end 200p and a distal end 200d and extending along a central longitudinal axis A1. The body 210 of the driver shaft 200 can be solid or can be cannulated to allow passage of a guidewire therethrough.

The driver shaft 200 can include one or more protrusions, bulges, or other areas of increased diameter 212. The protrusions 212 can be configured to support the extension tabs of a bone anchor as a fastener is applied to the bone anchor. Such protrusions 212 can help prevent the extension tabs from bending inward towards the body 210 and breaking off or separating from the bone anchor assembly prematurely. Alternatively, or in addition, the protrusions 212 can help align the instrument 100 and a fastener coupled thereto with the bone anchor, for example by centering the instrument between extension tabs of the bone anchor or within a tubular access device leading to the bone anchor.

The driver shaft 200 can include various markings 214 for guiding the user. For example, the driver shaft 200 can include a plurality of depth markings along its length to indicate to the user an inserted depth of the instrument 100. As another example, proximal and distal markings 214 can be formed on the driver shaft 200 to indicate the inserted depth at which a fastener first begins to engage a proximal end of a bone anchor and the inserted depth at which the fastener is fully seated in the bone anchor. The location of the markings 214 along the length of the driver shaft 200 can be calibrated to the length of an access device or extension tabs extending from the bone anchor with which the instrument 100 is to be used. The markings 214 can be formed on a protrusion 212 of the driver shaft 200 as shown, or can be formed at any other location along the driver shaft.

The driver shaft 200 can include a shoulder 204 for transferring an axially-directed force from the sliding handle 300 and locking collar 400 to the driver shaft. The illustrated shoulder is defined by a generally annular projection 204. The projection 204 defines a proximal-facing impact surface 216 configured to bear against the locking collar 400 when the handle 300 is slid distally along the driver shaft 200. The impact surface 216 can be planar or substantially planar as shown and can extend perpendicular or substantially perpendicular to the axis A1. The impact surface 216 can serve as a distal limit for longitudinal travel of the handle 300 and locking collar 400 relative to the driver shaft 200.

The assembly sleeve 206 can be attached at a proximal portion 218 of the driver shaft 200 to define a proximal limit for longitudinal travel of the handle 300 relative to the driver shaft and to retain the handle and locking collar 400 on the driver shaft once assembled. The sleeve 206 can be reversibly or non-reversibly secured to the driver shaft 200 in various ways. For example, the sleeve 206 can be welded or glued to the driver shaft 200, or the driver shaft can be press fit into a central passage of the sleeve.

The proximal end 200p of the driver shaft 200 can include a modular coupling 208 for selectively attaching the driver shaft to a structure or device for applying a rotational force to the driver shaft about the longitudinal axis A1. For example, the modular coupling 208 can be configured to attach the driver shaft 200 to a handle or knob configured to be grasped by a user, to a powered device such as an electric or pneumatic drill or driver, or to a surgical robot. In other embodiments, the driver shaft 200 can include a handle formed integrally therewith. Exemplary handles include pencil-type handles, palm-grip handles, T-handles, and the like.

A section of the driver shaft 200 extending between the shoulder 204 and the sleeve 206 can include one or more grooves, recesses, or other surface features to facilitate interaction with the handle 300 and the locking collar 400.

For example, the driver shaft 200 can include a non-cylindrical portion configured to be disposed within a corresponding non-cylindrical portion of the handle 300 to lock rotation of the handle relative to the driver shaft about the axis A1. In the illustrated embodiment, the driver shaft 200 includes opposed planar side surfaces 220 that engage with the handle 300, as described further below, to prevent rotation of the handle about the driver shaft.

As another example, the driver shaft 200 can include one or more recesses configured to receive a corresponding projection of the locking collar 400 to selectively secure the locking collar and the handle 300 coupled thereto at a fixed longitudinal position along the driver shaft. As shown, the driver shaft 200 can include a distal groove 222 for selectively locking the handle 300 in a distal position and a proximal groove 224 for selectively locking the handle in a proximal position. The grooves 222, 224 can be formed about less than an entire circumference of the driver shaft 200, e.g., in two discrete diametrically-opposed positions as shown. This can allow the locking collar 400 to engage the grooves 222, 224 when placed in a first rotational position about the driver shaft 200 to lock longitudinal translation and to disengage from the grooves when placed in a second rotational position about the driver shaft to permit longitudinal translation. The second rotational position can be offset from the first rotational position, e.g., by 90 degrees, 180 degrees, etc. The grooves 222, 224 can include a curved, tapered, or ramped lead-in surface 226 to facilitate positioning of the projections of the locking collar 400 within the grooves, e.g., to prevent binding when the projections are not precisely aligned with the grooves in the longitudinal direction. Interaction between the locking collar 400 and the driver shaft 200 is described further below.

As another example, the driver shaft 200 can include one or more reliefs 228 to permit an finger portions of the locking collar 400 to deform radially-inward towards the axis A1, as described further below.

The distal end 200d of the driver shaft 200 can include a drive tip 202 for engaging a corresponding drive interface of a fastener and for transferring rotational force applied to the driver shaft to the fastener. Exemplary drive tips include Phillips, slotted, hexalobe, Torx®, hexagonal, pentalobe, and the like, of various standard or non-standard sizes. The drive tip 202 can also include a modular connector such that any of a plurality of drive tips having different types or sizes can be selectively coupled to the distal end of the driver shaft 200. The drive tip 202 can be a static, solid, and/or monolithic structure.

The drive tip 202 can be tapered to help retain a fastener to the instrument 100. The drive tip 202 can taper from a reduced distal cross-section to an enlarged proximal cross-section. The drive tip 202 can be continuously tapered or can be stepped in the proximal-distal direction. The drive tip 202 can be tapered at one or more planar ramped portions. The drive tip 202 can be tapered at one or more concavely curved portions. The drive tip 202 can be conically tapered.

An exemplary drive tip 202 is shown in greater detail in FIGS. 2C-2E. The illustrated drive tip 202 includes a plurality of raised peaks 230 spaced about the circumference of the drive tip and separated by respective valleys 232. While a hexalobe drive geometry is shown, it will be appreciated that other geometries can be used instead or in addition, including geometries having any number of peaks and valleys. A longitudinal cross-section of the drive tip 202 can include a distal section 202D, an intermediate tapered section 202T, and a proximal section 202P.

The distal section 202D can include a first portion that is obliquely angled with respect to the axis A1 to define a lead-in surface 234 to facilitate insertion of the drive tip 202 into a fastener drive recess. The lead-in surface 234 can extend from the central axis A1 at an angle B1. The angle B1 can be in the range of about 30 degrees to about 60 degrees. The angle B1 can be about 45 degrees. The distal section 202D can include a second portion that is parallel to the axis A1.

The proximal section 202P can be concavely or convexly curved in one or more steps to transition from the outside diameter of a proximal end of the tapered section 202T to the outside diameter of the body 210 of the driver shaft 200.

The intermediate tapered section 202T can taper from a reduced distal cross section, e.g., a reduced distal diameter D1, to an enlarged proximal cross section, e.g., an enlarged proximal diameter D2. The tapered section 202T can be obliquely angled with respect to the axis A1 to define the taper. The tapered section 202T can extend from the central axis A1 at an angle B2. The angle B2 can be in the range of about 2 degrees to about 10 degrees. The angle B2 can be in the range of about 3 degrees to about 7 degrees. The angle B2 can be about 5 degrees. While a planar tapered surface is shown, the tapered surface can be curved, stepped, etc.

The protrusions 230 can be tapered along the intermediate section 202T, the valleys 232 can be tapered along the intermediate section 202T, or both the protrusions 230 and the valleys 232 can be tapered along the intermediate section 202T.

The length L1 between the distal-most end of the drive tip 202 and the proximal end of the intermediate tapered section 202T can be selected to correspond with the depth of the drive recess of the fastener with which the instrument 100 is to be used, such that at least a portion of the intermediate tapered section 202T is received within the drive recess when the drive tip 202 is seated in the drive recess. The drive recess can have a diameter that is greater than or equal to the diameter D1 and less than the diameter D2 such that an interference fit occurs between the intermediate tapered section 202T and the drive recess to frictionally retain the fastener on the instrument 100. While an arrangement is described herein in which a tapered drive tip is used with a non-tapered fastener recess, it will be appreciated that in other embodiments the fastener can include a tapered drive recess and the drive tip can be non-tapered.

Figure 2F:
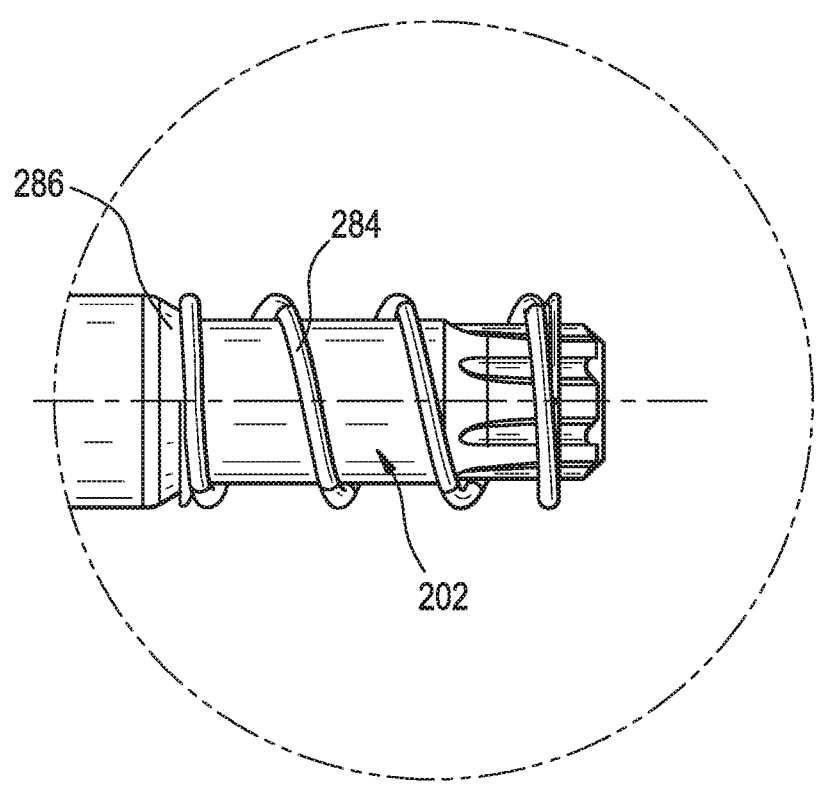
FIG. 2F is a detail side view of the drive tip FIG. 2C, shown with a release spring.
Figure 3A:
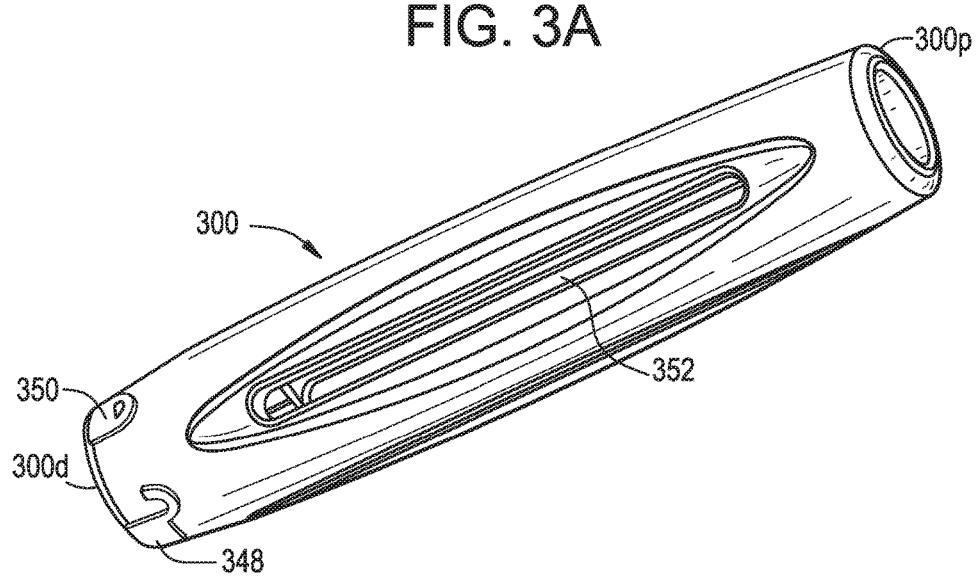
FIG. 3A is a perspective view of a handle of the instrument of FIG. 1A.
Figure 3B:
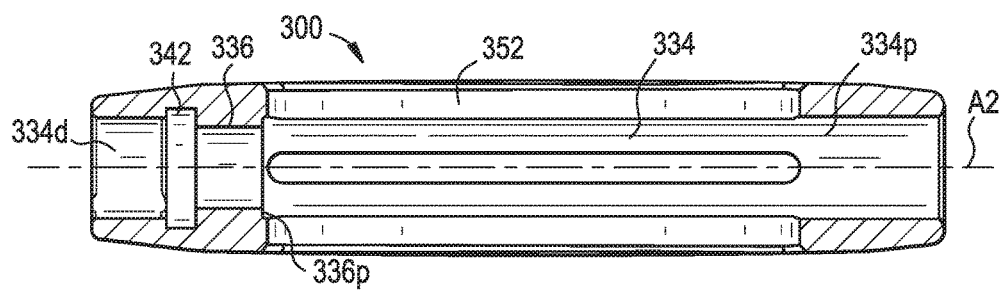
FIG. 3B is a sectional side view of the handle of FIG. 3A.
Figure 3C:
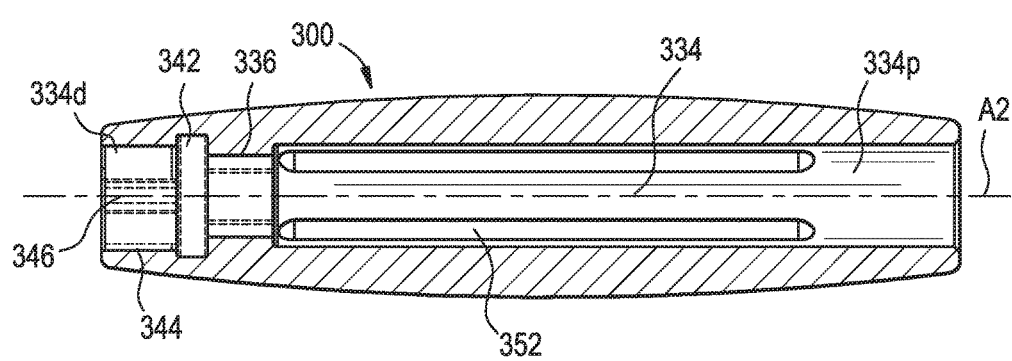
FIG. 3C is a sectional top view of the handle of FIG. 3A.
Figure 3D:
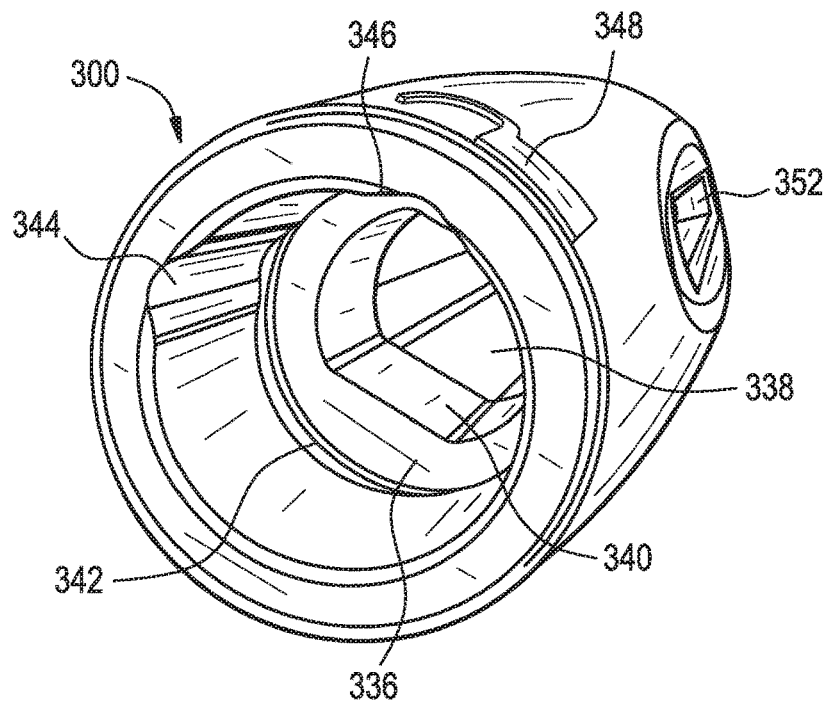
FIG. 3D is another perspective view of the handle of FIG. 3A.
Figure 3E:
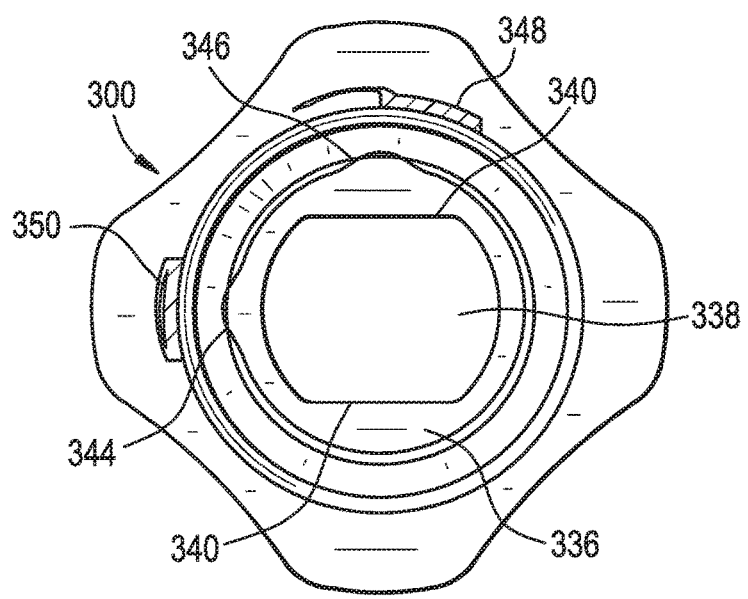
FIG. 3E is an end view of the handle of FIG. 3A.

The instrument 100 can include a release element to aid in releasing a fastener from the instrument. For example, as shown in FIG. 2F, the drive tip 202 can include a spring or bias element 284 configured to urge the drive tip out of engagement with a fastener coupled thereto. The spring 284 can be a coil spring as shown, or any of a variety of other structures configured to exert a release force on a fastener, such as leaf springs, wave springs, resilient compressible members, etc. The spring 284 can be disposed over an exterior surface of the drive tip 202. The spring 284 can be coaxially disposed with respect to the drive tip 202. The spring can be disposed within a central lumen of the drive tip 202. A proximal end of the spring 284 can bear against a shoulder 286 of the drive tip. A distal end of the spring 284 can be configured to bear against a fastener when the fastener is coupled to the drive tip 202. The spring 284 can bear directly against the fastener, or can include a distal plunger that bears against the fastener. In use, the spring 284 can urge the fastener out of engagement with the drive tip 202, e.g., to help release the fastener from the instrument after the fastener is tightened to an implanted construct.

The handle 300 is shown in greater detail in FIGS. 3A-3E. As shown, the handle 300 can include an elongate, generally-cylindrical body having a proximal end 300p and a distal end 300d and extending along a central longitudinal axis A2. The handle 300 can define a central passage 334 extending between the proximal and distal ends 300p, 300d. The driver shaft 200 can be coaxially received within the central passage 334, such that the central axis A2 of the handle 300 is collinear with the central axis A1 of the driver shaft 200.

The handle 300 can include features for preventing relative rotation between the handle and the driver shaft 200. For example, proximal and distal portions 334p, 334d of the central passage 334 can be separated by a dividing wall 336. The dividing wall 336 can define an opening 338 having a shape configured to prevent rotation of the handle 300 relative to the driver shaft 200 about the axis A2. In the illustrated embodiment, the opening 338 has opposed planar sidewalls 340 configured to engage the opposed planar side surfaces 220 of the driver shaft 200. Various other features for preventing relative rotation can be used instead or in addition, including a ridge-and-groove coupling, one or more transverse pins, etc. A proximal-facing surface 336p of the dividing wall 336 can be configured to contact and bear against the assembly sleeve 206 to limit proximal translation of the handle 300 along the driver shaft 200.

The handle 300 can include features for selectively attaching the locking collar 400 to the handle such that the handle and the locking collar are longitudinally fixed to one another but remain free to rotate relative to one another about the axis A2. For example, the distal portion 334d of the central passage 334 can include an annular groove 342 formed in an interior sidewall of the passage. The groove 342 can receive one or more fingers of the locking collar 400, as described further below, to couple the locking collar to the handle 300.

The handle 300 can include features for providing an indication to a user as to whether the handle is in a locked or an unlocked configuration. The illustrated handle 300 includes first and second longitudinal grooves or dimples 344, 346 formed in the distal portion 334d of the central passage 334 and spaced about the circumference of the handle. The grooves 344, 346 can be configured to selectively receive an indicator finger of the locking collar 400, as described further below, to provide tactile feedback to a user when the locking collar is positioned in a locked or an unlocked configuration. The grooves 344, 346 can also provide resistance to rotation of the locking collar 400 out of the locked or unlocked configurations, e.g., to prevent inadvertent movement of the locking collar and limit movement out of the locked or unlocked configuration to situations where it is specifically intended by the user. The handle 300 can include external markings 350, 348, which can be aligned with the grooves 344, 346 as shown, to provide a visual indication to the user as to the location of the groove 344 associated with the locked configuration and the location of the groove 346 associated with the unlocked configuration. The markings 348, 350 can be stamped, printed, or otherwise formed on an exterior surface of the handle. In the illustrated embodiment, a closed padlock symbol 350 is used to mark the location about the circumference of the handle 300 of the locked configuration groove 344 and an open padlock symbol 348 is used to mark the location about the circumference of the handle of the unlocked configuration groove 346.

One or more openings 352 can be formed in the sidewall of the handle 300, which can advantageously allow sterilizing solutions, cleaning agents, or other flowable materials to access the interior of the handle. The illustrated handle 300 includes a plurality of elongate slits 352 that are open to the central passage 334 and spaced about the circumference of the handle.

The handle 300 can include features to facilitate gripping of the handle and application of torque thereto, such as textured surfaces, faceted surfaces, knurling, grooved surfaces, etc. By way of further example, as shown in FIGS. 3F-3G, the handle 300 can include one or more deployable hinged levers or handle arms 388. The arms 388 can be positioned in a retracted or stowed position, e.g., as shown in FIG. 3F, and can be selectively moved to a deployed position, e.g., as shown in FIG. 3G. The arms 388 in the deployed position may provide better user ergonomics and/or enhance the amount of torque that a user can apply with the instrument 100. The arms 388 can have longitudinal axes that are parallel or substantially parallel to the longitudinal axis of the handle 300 in the retracted position and perpendicular or substantially perpendicular to the longitudinal axis of the handle 300 in the deployed position. While two arms 388 are shown, the handle 300 can include any number of arms. In one arrangement, the handle 300 can include a single arm 388 configured to project radially-outward from one side of the handle 300 to form an L-shaped handle. In another arrangement, the handle 300 can include a single arm 388 configured to project radially-outward from two opposed sides of the handle 300 to form a T-shaped handle. In another arrangement, as shown, the handle 300 can include first and second arms 388 configured to project radially-outward from two opposed sides of the handle 300 to form a T-shaped handle. In the stowed position, the arms 388 can be nested in the handle 300. For example, the arms 388 can be partially or completely disposed within pockets or recesses formed in the handle 300. The arms 388 can be pivotally coupled to the handle, e.g., via respective pivot pins as shown, via a hinge structure, or via any of a variety of other joint mechanisms. The arms 388 can include retention features to help retain the arms in the deployed or retracted positions or locking features to lock the arms in the deployed or retracted positions.

Figure 4A:
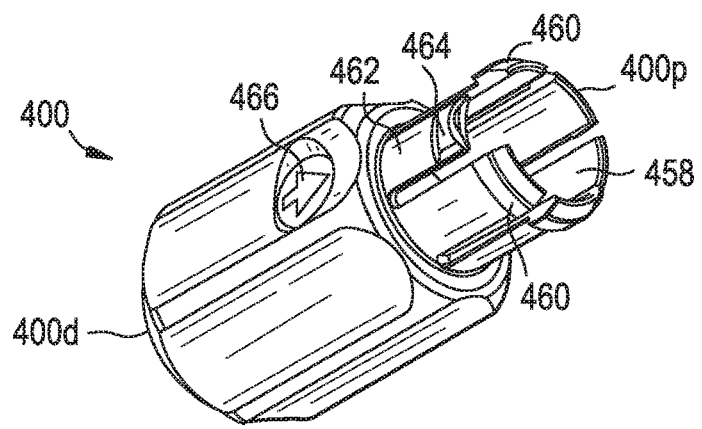
FIG. 4A is a perspective view of a locking collar of the instrument of FIG. 1A.
Figure 4B:
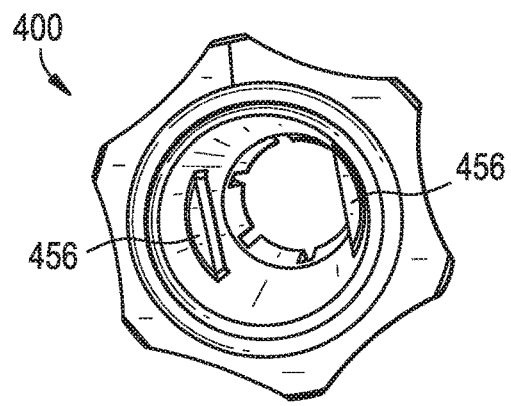
FIG. 4B is another perspective view of the locking collar of FIG. 4A.
Figure 4C:
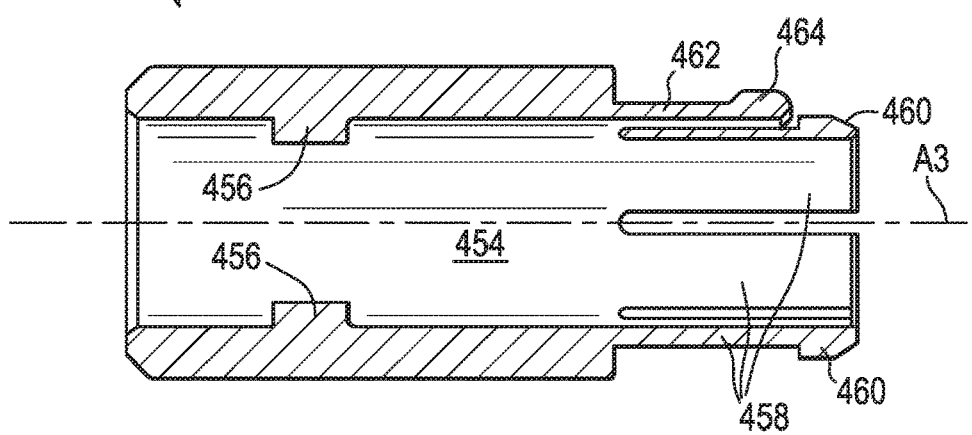
FIG. 4C is a sectional side view of the locking collar of FIG. 4A.

The locking collar 400 is shown in greater detail in FIGS. 4A-4C. As shown, the locking collar 400 can include an elongate, generally-cylindrical body having a proximal end 400p and a distal end 400d and extending along a central longitudinal axis A3. The locking collar 400 can define a central passage 454 extending between the proximal and distal ends 400p, 400d. The driver shaft 200 can be coaxially received within the central passage 454, such that the central axis of the locking collar A3 is collinear with the central axis A1 of the driver shaft 200.

The locking collar 400 can include features for selectively preventing longitudinal translation of the locking collar and the handle 300 coupled thereto relative to the driver shaft 200. For example, the locking collar 400 can include one or more projections 456 that extend radially inward from an inner sidewall of the central passage 454. The projections 456 can be received within corresponding recesses 222, 224 of the driver shaft 200 to selectively secure the locking collar 400 and the handle 300 coupled thereto at a fixed longitudinal position along the driver shaft. The projections 456 can be formed about less than an entire circumference of the locking collar 400, e.g., in two discrete diametrically-opposed positions as shown. This can allow the projections 456 to be received within the grooves 222, 224 of the driver shaft 200 when placed in a first rotational position about the driver shaft to lock longitudinal translation, and to disengage from the grooves 222, 224 when placed in a second rotational position about the driver shaft to permit longitudinal translation.

The locking collar 400 can include features for selectively attaching the locking collar to the handle 300 such that the handle and the locking collar are longitudinally fixed to one another but remain free to rotate relative to one another about the axis A3. For example, the locking collar 400 can include one or more retention fingers 458 extending proximally therefrom. The fingers 458 can include projections 460 extending radially outward from an outer surface of the fingers and configured to be received within the annular groove 342 of the handle 300. When the projections 460 are received within the groove 342, a distal-facing surface of the projections can bear against a proximal-facing surface of the groove to prevent distal movement of the locking collar 400 relative to the handle 300. The distal-facing surface of the projections 460 and the proximal-facing surface of the groove 342 can be planar as shown and can extend perpendicular to the axis A3. When the projections 460 are received within the groove 342, a proximal-facing surface of the locking collar 400 can bear against a distal-facing surface of the handle 300 to prevent proximal movement of the locking collar relative to the handle. The proximal-facing surface of the locking collar 400 and the distal-facing surface of the handle 300 can be planar as shown and can extend perpendicular to the axis A3. Proximal-facing surfaces of the protrusions 460 can extend at an oblique angle with respect to the axis A3 to define ramped lead-in surfaces. As the fingers 458 are inserted into the distal portion 334d of the central passage 334 of the handle 300, the ramped surfaces can engage the handle and cause the fingers to deform radially inward towards the axis A3. The fingers 458 can be formed from a resilient material such that, once the projections 460 are aligned with the groove 342 of the handle 300, the fingers automatically deform radially outward to position the projections within the groove. While a locking collar 400 having five retention fingers 458 spaced about a circumference of the locking collar is shown, it will be appreciated that the locking collar can include any number of retention fingers, or can include different features for retaining the collar to the handle 300 while permitting relative rotational movement therebetween.

The locking collar 400 can include features for providing an indication to a user as to whether the handle 300 is in a locked or an unlocked configuration. The illustrated locking collar 400 includes an indicator finger 462 having a projection 464 extending radially-outward therefrom configured to be selectively received within one of the first and second longitudinal grooves 344, 346 formed in the handle 300. The indicator finger 462 can provide tactile feedback to a user when the locking collar 400 is positioned in a locked or an unlocked configuration. The indicator finger 462 can also provide resistance to rotation of the locking collar 400 out of the locked or unlocked configurations, e.g., to prevent inadvertent movement of the locking collar and limit movement out of the locked or unlocked configuration to situations where it is specifically intended by the user. The indicator finger 462 can be longer or shorter than the retention fingers 458 such that the projection 464 is axially-offset from the annular groove 342 of the handle 300 when the locking collar 400 is assembled to the handle. The indicator finger 462 can be formed from a resilient material such that the projection 464 snaps into engagement with the first or second longitudinal grooves 344, 346 of the handle 300 when the indicator finger is rotationally-aligned with said grooves. Lateral extents of the projection 464 can be convexly curved as shown to facilitate insertion and removal of the projection from the grooves 344, 346. Similarly, lateral extents of the grooves 344, 346 can be concavely curved to facilitate such insertion and removal. The indicator finger 462 can be received within one of the reliefs 228 formed in the driver shaft 200 as the indicator finger is deflected radially-inward during movement into and out of engagement with the first and second grooves 344, 346. While a single indicator finger 462 is shown, it will be appreciated that the locking collar 400 can include any number of indicator fingers, or can include different features for engaging the grooves 344, 346 of the handle 300.

The locking collar 400 can include an external marking 466, which can be aligned with the indicator finger 462 as shown, to provide a visual indication to the user as to the location of the indicator finger. The marking 466 can be stamped, printed, or otherwise formed on an exterior surface of the locking collar 400. In the illustrated embodiment, an arrow symbol 466 is used to mark the location about the circumference of the locking collar 400 of the indicator finger 462.

The indicator finger 462 can be positioned relative to the projections 456 and the grooves 344, 346 can be positioned relative to the recesses 222, 224 such that, when the indicator finger 462 is received within the first or "locked" groove 344, the projections 456 are received within the recess 222 or the recess 224 to lock the longitudinal position of the handle 300 and such that, when the indicator finger 462 is received within the second or "unlocked" groove 346, the projections 456 are positioned outside of the recess 222 and the recess 224 to allow longitudinal movement of the handle 300 along the driver shaft 200.

An exterior surface of the locking collar 400 can include features to facilitate gripping and rotation of the locking collar by a user. For example, the exterior surface can include a plurality of longitudinally-extending cylindrical depressions as shown. The depressions can define raised ridges therebetween for gripping by a user.

A distal-facing surface of the locking collar 400 can be configured to contact and bear against the shoulder 204 of the driver shaft 200 to limit distal translation of the locking collar and the handle 300 along the driver shaft and to apply an axially-directed force to the driver shaft.

While the illustrated instrument 100 includes a locking collar 400 disposed distal to the handle 300, it will be appreciated that in other arrangements the locking collar can be proximal to the handle or can be disposed at an intermediate location along the handle.

In use, the instrument 100 can be provided initially in a completely assembled state, or can be assembled by the end user. Assembly of the instrument 100 can be completed by inserting the proximal end of the locking collar 400 into the distal end of the handle 300 until the retention fingers 458 spring into engagement with the annular groove 342 of the handle. The proximal end of the driver shaft 200 can then be inserted into the distal end of the locking collar 400 to position the locking collar and the handle 300 over the driver shaft. The assembly sleeve 206 can then be attached to the driver shaft 200 to retain the locking collar 400 and the handle 300 on the driver shaft.

The instrument 100 can be used to apply a fastener to a bone anchor, such as a pedicle or lateral mass screw implanted in a spine of a patient. The fastener can be loaded onto the instrument as shown in FIGS. 5A-5E and applied to a bone anchor as shown in FIGS. 5F-5I.

Figure 5A:
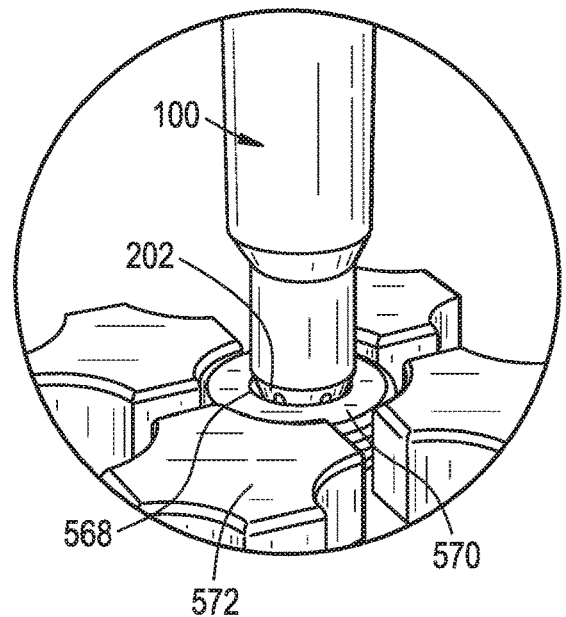
FIG. 5A is a perspective view of the drive tip of the instrument of FIG. 1A partially inserted into a bone anchor fastener mounted in a fastener caddy.
Figure 5B:
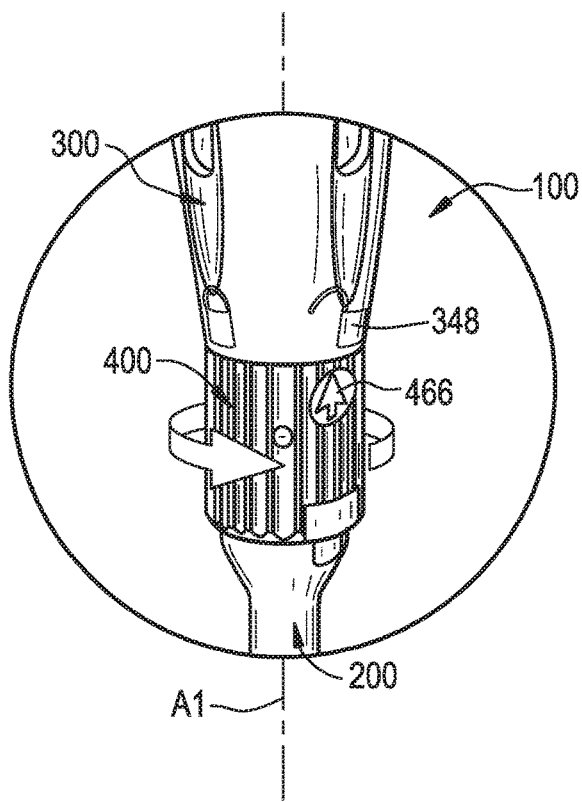
FIG. 5B is a perspective view of the locking collar of the instrument of FIG. 1A rotated to an unlocked position.

The drive tip 202 of the instrument 100 can be positioned within a corresponding drive recess 568 of a fastener 570, as shown in FIG. 5A. The fastener 570 can be a set screw as shown, and can be supplied in a caddy or other case 572 that holds the fastener during shipping, sterilization, or other processes. Next, the instrument 100 can be actuated to impact the drive tip 202 distally into the drive recess 568 of the fastener 570. As shown in FIG. 5B, the handle 300 can be positioned in an unlocked position by rotating the locking collar 400 relative to the handle about the axis A1. In the unlocked position, the visual indicator 466 of the locking collar 400 is aligned with the visual "unlocked" indicator 348 of the handle 300, the indicator finger 462 of the locking collar 400 is received within the "unlocked" groove 346 of the handle 300, and the projections 456 of the locking collar 400 are rotationally offset from the recesses 222, 224 of the driver shaft 200, allowing free longitudinal translation of the handle and locking collar relative to the driver shaft. With the instrument in the unlocked configuration, the handle 300 can be "slapped," dropped under the force of gravity, or otherwise forcibly moved distally as shown in FIG. 5C to impact the locking collar 400 against the shoulder 204 of the driver shaft 200 and thereby exert an axially-directed force onto the driver shaft to impact the drive tip 202 into the fastener 570. The force can be effective to press tapered surfaces or other retention features of the drive tip 202 and/or fastener 570 into engagement with one another to releasably secure the fastener to the instrument 100. The weight of the handle 300 and the locking collar 400 can be calibrated to reliably and repeatedly retain the fastener 570 to the drive tip 202 when the handle is dropped from a proximal-most position to a distal-most position.

With the fastener 570 loaded onto the instrument 100, the instrument can be moved to an initial insertion configuration. For example, as shown in FIGS. 5D and 5E, the handle 300 and the locking collar 400 can be slid proximally along the driver shaft 200 and locked in place in a proximal position along the driver shaft. The handle 300 can be positioned in a locked position by rotating the locking collar 400 relative to the handle about the axis A1. In the locked position, the visual indicator 466 of the locking collar 400 is aligned with the visual "locked" indicator 350 of the handle 300, the indicator finger 462 of the locking collar 400 is received within the "locked" groove 344 of the handle 300, and the projections 456 of the locking collar 400 are received within the proximal groove 224 of the driver shaft 200 to prevent longitudinal translation of the handle and the locking collar relative to the driver shaft.

Figure 5F:
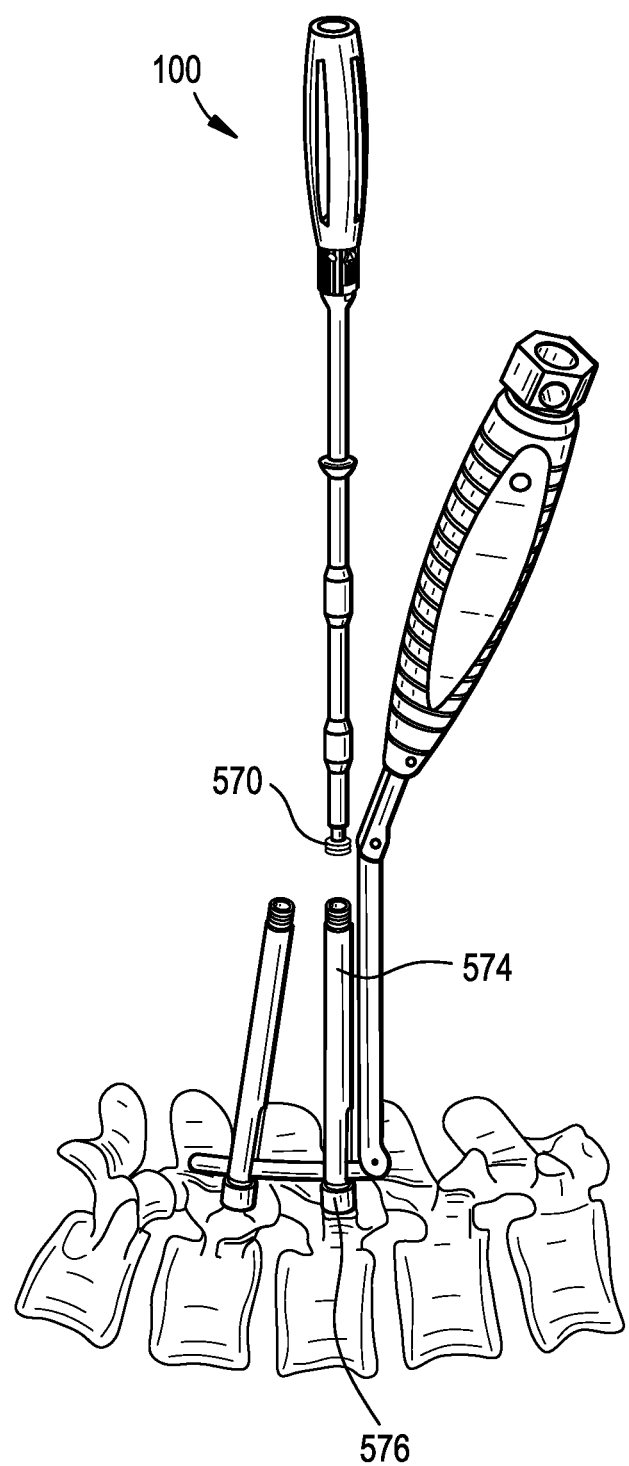
FIG. 5F is a perspective view of the instrument of FIG. 1A being used to apply a fastener to a bone anchor implanted in a human spine.

In the initial insertion configuration, the pencil-type handle 300 can provide an ergonomic geometry for the user to insert the fastener 570 into a bone anchor and quickly advance the fastener along threads of the bone anchor while minimal torque input is required. For example, the instrument 100 can be used to guide the fastener 570 through a minimally-invasive percutaneous access device 574 towards a bone anchor 576 implanted in a patient's spine, as shown in FIG. 5F. Retention of the fastener 570 onto the drive tip of the instrument 100 can advantageously reduce the risk of dropping the fastener down into the access device 574. As shown in FIG. 5G, the instrument 100 in the initial insertion configuration can be used to quickly and ergonomically advance the fastener 570 along the threads of the reduction tabs 578 and/or the receiver head 580 of the bone anchor 576.

When final tightening of the fastener 570 is to be performed, when increased torque is required, or at any other time desired by the user, the instrument 100 can be moved to a final tightening configuration as shown in FIGS. 5H-5I. For example, the handle 300 can be unlocked as described above and advanced distally along the driver shaft 200 to expose the modular coupling 208 of the driver shaft. The handle 300 can be locked in the distal position by rotating the locking collar 400 as described above such that the projections 456 of the locking collar are received within the distal recess 222 of the driver shaft 200. A T-handle 582, powered driver, or other component for applying high levels of torque can be attached to the modular coupling 208, as shown in FIG. 5I. The instrument 100 can then be rotated to apply final tightening torque to the fastener 570 received within the bone anchor 576. The instrument 100 can be used with compression or distraction instruments before or during final tightening to achieve a desired correction or relative vertebral position.

With the fastener 570 in its final position with respect to the bone anchor 576, or at any other desired time, the instrument 100 can be separated from the fastener by applying an axially directed force to the driver shaft 200 in a proximal direction. This can be achieved, for example, by simply pulling the instrument 100 proximally. Or, if separation from the fastener 570 is difficult, the handle 300 can be "slapped" or forcibly impacted proximally against the assembly sleeve 206 to release the fastener 570.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

It will be appreciated from the foregoing that the instrument 100 can allow fastener loading, initial insertion, intermediate tightening, and final torqueing to be performed with a single instrument without ever having to release the fastener from the instrument. It will further be appreciated that the instrument 100 can provide a simple and reliable way of loading the fastener and retaining the fastener to prevent dropping while at the same time being strong enough to apply the high levels of torque typically required for final tightening a spinal fixation construct, e.g., at least about 80 inch pounds.

The instruments disclosed herein can be constructed from any of a variety of known materials. Exemplary materials include those which are suitable for use in surgical applications, including metals such as stainless steel, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of advancing a fastener into a bone anchor implanted in a bone such as the pedicle or lateral mass of a human spine, it will be appreciated that the methods and devices disclosed herein can be used with any human or animal bone, implant, non-living object, and so forth.

Although specific embodiments are described above, it should be understood that numerous changes may be made within the spirit and scope of the concepts described.

The invention claimed is:

1. A method of applying a fastener to a bone anchor, comprising:
   inserting a drive tip of a driver instrument into a drive recess of the fastener;
   applying an axial force to a driver shaft of the instrument to impact the drive tip into the drive recess of the fastener and retain the fastener to the drive tip by an interference fit;
   sliding a handle of the instrument along a longitudinal axis of the driver shaft;
   positioning the instrument and the fastener retained thereto with respect to a bone anchor; and
   rotating the driver shaft to apply the fastener to the bone anchor,
   wherein the fastener is a set screw and wherein applying the fastener comprises threading the set screw into opposed threaded arms the bone anchor to retain a spinal rod within the bone anchor.

2. The method of claim 1, wherein applying the axial force comprises sliding the handle of the instrument distally along the driver shaft to exert an axial force on a shoulder of the driver shaft.

3. The method of claim 1, wherein retaining the fastener comprises wedging a tapered portion of the drive tip within the drive recess of the fastener.

4. The method of claim 3, wherein the tapered portion tapers continuously from a reduced distal diameter to an enlarged proximal diameter, and wherein the drive recess of the fastener has a diameter that is greater than or equal to the reduced distal diameter and less than the enlarged proximal diameter.

5. The method of claim 1, further comprising locking the handle at a fixed longitudinal position along the driver shaft.

6. The method of claim 5, wherein locking the handle comprises rotating a locking collar coupled to the handle with respect to the handle about a central longitudinal axis of the driver shaft to a locked position.

7. The method of claim 6, wherein, when the locking collar is in the locked position, a projection formed in a central passage of the locking collar is received within a corresponding recess formed in the driver shaft to prevent longitudinal translation of the locking collar relative to the driver shaft.

8. The method of claim 7, wherein, when the locking collar is in the locked position, an indicator finger of the locking collar is received within a groove formed in the handle to maintain the locking collar in the locked position and provide an indication to a user that the locking collar is in the locked position.

9. The method of claim 5, further comprising unlocking the handle from a fixed longitudinal position along the driver shaft.

10. The method of claim 9, wherein unlocking the handle comprises rotating a locking collar coupled to the handle with respect to the handle about a central longitudinal axis of the driver shaft to an unlocked position.

11. The method of claim 10, wherein, when the locking collar is in the unlocked position, a projection formed in a central passage of the locking collar is positioned outside of a corresponding recess formed in the driver shaft to allow longitudinal translation of the locking collar relative to the driver shaft.

12. The method of claim 11, wherein, when the locking collar is in the unlocked position, an indicator finger of the locking collar is received within a groove formed in the handle to maintain the locking collar in the unlocked position and provide an indication to a user that the locking collar is in the unlocked position.

13. The method of claim 1, further comprising rotating a locking collar of the instrument to lock or unlock a longitudinal position of the handle with respect to the driver shaft, wherein rotating the locking collar comprises rotating a plurality of retention fingers extending from the locking collar within an annular groove formed in the handle.

14. The method of claim 1, further comprising, without separating the driver shaft from the fastener, sliding the handle to a distal position along the driver shaft, attaching a second handle to a proximal end of the driver shaft, and rotating the second handle to further tighten the fastener to the bone anchor.

15. A method of applying a fastener to a bone anchor, comprising:
   inserting a drive tip of a driver instrument into a drive recess of the fastener;
   applying an axial force to a driver shaft of the instrument to impact the drive tip into the drive recess of the fastener and retain the fastener to the drive tip by an interference fit;
   positioning the instrument and the fastener retained thereto with respect to a bone anchor;
   rotating a handle of the instrument to rotate the driver shaft and apply the fastener to the bone anchor; and
   locking the handle at a fixed longitudinal position along the driver shaft;
   wherein locking the handle comprises rotating a locking collar coupled to the handle with respect to the handle about a central longitudinal axis of the driver shaft to a locked position;
   wherein, when the locking collar is in the locked position, a projection formed in a central passage of the locking collar is received within a corresponding recess formed in the driver shaft to prevent longitudinal translation of the locking collar relative to the driver shaft.

16. The method of claim 15, wherein, when the locking collar is in the locked position, an indicator finger of the locking collar is received within a groove formed in the handle to maintain the locking collar in the locked position and provide an indication to a user that the locking collar is in the locked position.

17. A method of applying a fastener to a bone anchor, comprising:
   inserting a drive tip of a driver instrument into a drive recess of the fastener;
   applying an axial force to a driver shaft of the instrument to impact the drive tip into the drive recess of the fastener and retain the fastener to the drive tip by an interference fit;
   positioning the instrument and the fastener retained thereto with respect to a bone anchor;
   rotating a handle of the instrument to rotate the driver shaft and apply the fastener to the bone anchor; and
   rotating a locking collar of the instrument to lock or unlock a longitudinal position of the handle with respect to the driver shaft, wherein rotating the locking collar comprises rotating a plurality of retention fingers extending from the locking collar within an annular groove formed in the handle.

* * * * *